United States Patent
Kolen et al.

(10) Patent No.: US 10,140,779 B2
(45) Date of Patent: Nov. 27, 2018

(54) CAMERA-BIOMETRIC MOTION TIMER AND METHOD

(71) Applicants: Paul T. Kolen, Encinitas, CA (US); John Andrew Wells, Paradise Valley, AZ (US)

(72) Inventors: Paul T. Kolen, Encinitas, CA (US); John Andrew Wells, Paradise Valley, AZ (US)

(73) Assignee: JAWKU L.L.C., Paradise Valley, AZ (US)

( * ) Notice: Subject to any disclaimer, the term of this patent is extended or adjusted under 35 U.S.C. 154(b) by 148 days.

(21) Appl. No.: 15/330,216

(22) PCT Filed: Jan. 13, 2016

(86) PCT No.: PCT/US2016/013145
§ 371 (c)(1),
(2) Date: Aug. 25, 2016

(87) PCT Pub. No.: WO2016/160091
PCT Pub. Date: Oct. 6, 2016

(65) Prior Publication Data
US 2017/0243407 A1  Aug. 24, 2017

Related U.S. Application Data

(60) Provisional application No. 62/178,034, filed on Mar. 31, 2015, provisional application No. 62/282,571, filed on Aug. 5, 2015.

(51) Int. Cl.
*G01C 22/00* (2006.01)
*G07C 1/24* (2006.01)
(Continued)

(52) U.S. Cl.
CPC ............. *G07C 1/24* (2013.01); *A61B 5/00* (2013.01); *A61B 5/11* (2013.01); *A61B 5/681* (2013.01); *G01S 19/51* (2013.01); *G04F 10/00* (2013.01); *G06F 3/0346* (2013.01); *H04N 5/23203* (2013.01); *H04N 5/44* (2013.01); *H04N 2201/3253* (2013.01)

(58) Field of Classification Search
CPC .......... G01C 22/006; G01C 22/00; A43B 3/00
USPC ........................................................ 235/105
See application file for complete search history.

(56) References Cited

U.S. PATENT DOCUMENTS 9,375,627 B2 * 6/2016 Hansen .................... G07C 1/24
9,704,412 B2 * 7/2017 Wells ................. G09B 19/0038
(Continued)

*Primary Examiner* — Ahshik Kim

(57) ABSTRACT

An athlete measures sprint time by locating a smartphone having a camera and clock start button which is first activated at the finish line. The sprint end time is recorded by a photo stamp time app. This sprint end time activates a video trigger causing the smartphone to send a RF stop event signal to a wrist mounted motion sensor worn by the athlete. A sensor timer is started via the start event by track or self starting. In track starting, the athlete pushes a start button on the sensor to initiate a variable 2-5 second delayed sound READY-SET-GO series of beeps to start the sprint. In self starting, the sensor detects threshold motion parameters of the sprinter's start which activates the sensor's free running clock and saves the start time. The time base on the sensor is used to calculate run time.

20 Claims, 5 Drawing Sheets

(51) Int. Cl.
*G01S 19/51* (2010.01)
*G04F 10/00* (2006.01)
*G06F 3/0346* (2013.01)
*H04N 5/232* (2006.01)
*A61B 5/00* (2006.01)
*A61B 5/11* (2006.01)
*H04N 5/44* (2011.01)

(56) References Cited

U.S. PATENT DOCUMENTS

| | | | |
|---|---|---|---|
| 9,883,332 B2* | 1/2018 | Hansen | H04W 4/02 |
| 2010/0295943 A1* | 11/2010 | Cha | G01S 13/82 |
| | | | 348/143 |
| 2015/0335947 A1* | 11/2015 | Kaushansky | A63B 24/0062 |
| | | | 340/870.07 |

* cited by examiner

CAMERA-BIOMETRIC MOTION TIMER AND METHOD

CROSS-REFERENCE TO RELATED APPLICATION/INCORPORATED BY REFERENCE

This application makes reference to and incorporates in its entirety by reference U.S. patent application Ser. No. 14/121,226 filed Aug. 14, 2014, now US2015-0287338A1 and entitled "BIOMETRIC DATA GATHERING". The present application also claims the priority dates of and incorporates by reference in their entirety Provisional Applications 62/178,034, filed Mar. 31, 2015, entitled "Clap-Sync Timers and Method" and 62/282,571, filed Aug. 5, 2015, and entitled "Camera-Biometric Motion Timer and Method".

FIELD OF THE INVENTION

The present invention relates to a method by which a sole athlete can accurately time a premeasured distance traversed by the athlete using a prepositioned mobile smart device, such as a smartphone, and a wrist mounted 6-DOF mems type motion sensor such as that developed by JAWKU, L.L.C, a Delaware Company.

BACKGROUND OF THE INVENTION

Often an athlete in training is clocked for the time taken to cover a premeasured distance which entails a starting signal to start timing of the event and an end signal to stop timing the event. The starting signal may be an audible sound or series of sounds, such as a whistle, beep, siren or shot sound. For an end signal, a trainer may use a stop clock or a camera with a time stamp to determine the end of the event. This invention concerns a method and apparatus for training by which the athlete no longer needs a second person to clock the time taken to cover the predetermined distance thus providing maximum scheduling flexibility for the training time.

A previous method, disclosed in Provisional Application 62/178,034, for an athlete to self time a sprint was developed by the inventors of the present invention which relied on a "slap-sync" that simultaneously created a sync time base impulse for the wrist motion sensor via a slapping or mechanical sound being made, and an acoustic impulse for the smartphone app via the phone's microphone. These two simultaneous events synchronized both time bases. The run time was then determined by subtracting the start time recorded on the sensor from the stop event recorded by the video smartphone app.

It turned out that due to the two time bases being slightly different due to the tolerance of the crystal time base, the sync would drift as a function of total run time. To mitigate this drift, in ms/s, the drift was determined by a short calibration routine so the drift component of the measured time could be subtracted. This approach was acceptable but due to non-linearities in the drift, the Allen variance, the accuracy would degrade with time requiring the two time bases to be re-synced by another "slap-sync" which introduced a new run calibration burden. This was inconvenient for the user. As an object of the present invention, a new synchronization approach has been developed that relies on a single time base on the sensor only, eliminating the drift and the need for recurring re-sync via the "slap-sync" method.

BRIEF SUMMARY OF THE INVENTION

The motion sensor worn on the wrist has a timer started via the start event. The athlete has the option of selecting either track starting or self starting. A stop event is generated by the photo stamp time app. When the athlete passes the video trigger on the smartphone app, the smartphone transmits a RF (Radio Frequency) stop request to the sensor to cause the sensor to save the time value on receipt of the RF request. The difference in the start time recorded by the start event and the stop time event recorded by the sensor on receipt of the RF request equals the run time. There is an undetermined delay between when the video trigger is generated and the RF stop request is actually sent via the BLE (Bluetooth Low Energy) interface of the smartphone to the sensor of up to 0-20 ms. This is unavoidable due to the smartphone's OS (Operating System) not being real time. By using the "slap-sync" method previously employed this delay can be determined at the factory manufacturing the motion sensor sparing the user from having to re-sync. The delay is subtracted from the measured sprint time. By performing a large number of trials at the factory, the average delay and the SD (Standard Deviation) of the delay can be characterized. The average value of the characterized delay determined at the factory is subtracted from the measured sprint time, leaving only the residual SD as the error which need be done only once at the factory.

BRIEF DESCRIPTION OF THE DRAWINGS

Further features and advantages of the present invention will be apparent upon consideration of the following detailed description of the present invention, taken in conjunction with the following drawings, in which like references refer to like parts, and in which.

DETAILED DESCRIPTION OF THE INVENTION

Figure 1:
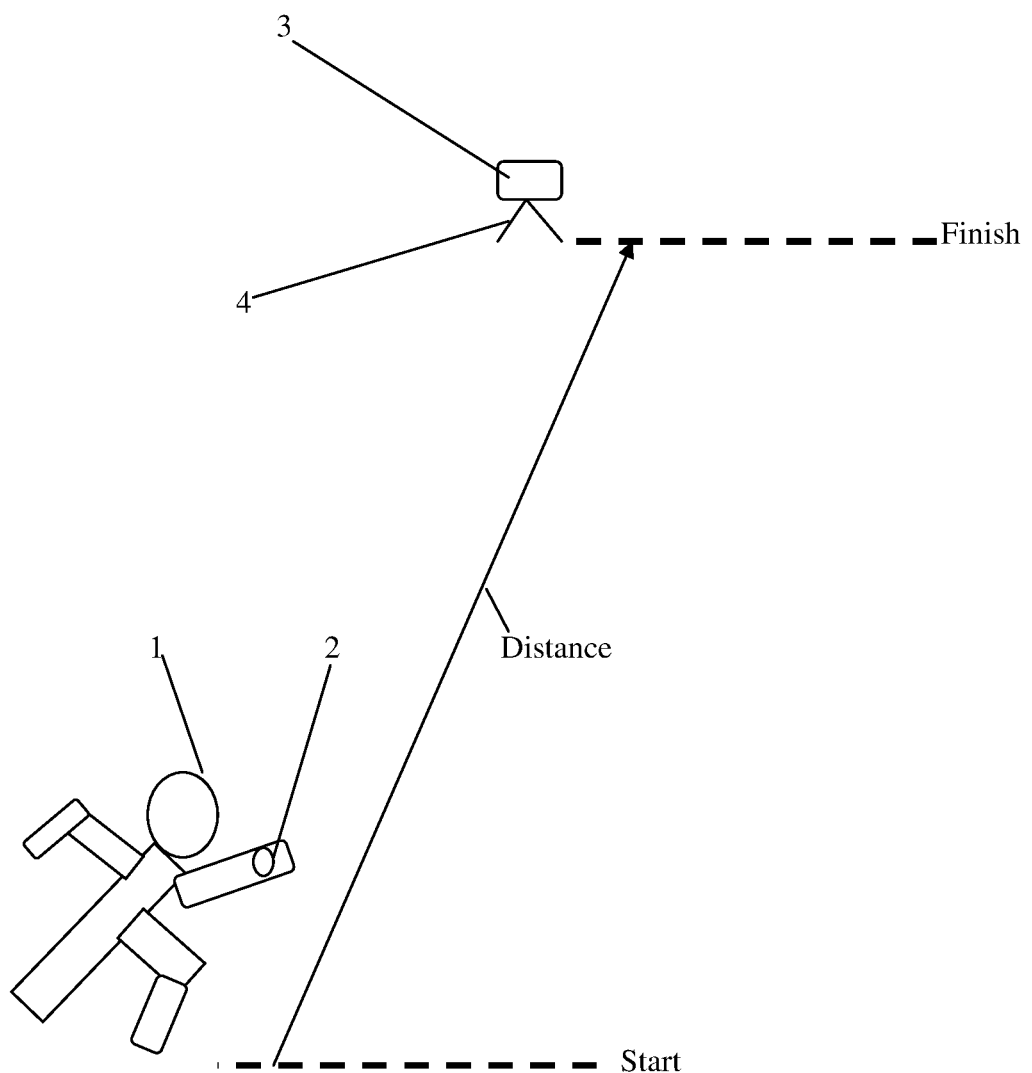
FIG. 1 schematically shows (not to scale) an athlete preparing to start to run a premeasured distance.
Figure 2:
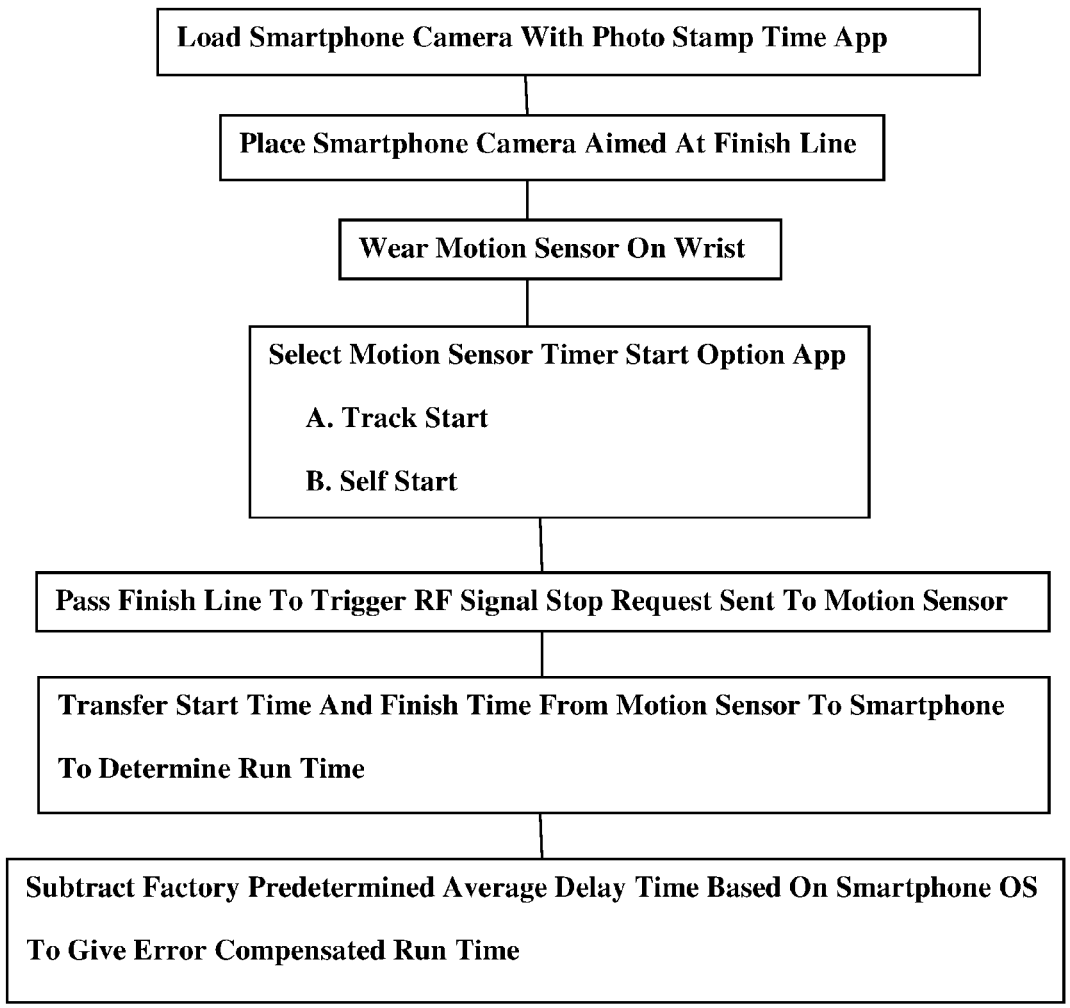
FIG. 2 depicts a flow chart of how the error compensated run time is obtained.

Referring to FIG. 1, an athlete 1 is starting to traverse a premeasured or predetermined distance, such as a 40 yard sprint. The athlete has previously prepositioned a smart device, such as a smartphone 3, on a tripod 4. The smartphone 3 has a camera which is aligned with the finish line of the predetermined distance. Referring to FIG. 2, a photo stamp time app is loaded into the smartphone to capture the finish time when the athlete crosses the finish line. At that time, a video trigger on the smartphone app causes the smartphone to send a RF stop request to a motion timer of a universal motion sensor 2 which is wrist mounted on the athlete as shown in FIG. 1. The smartphone has a crystal oscillator clock. The motion sensor 2 has a free running clock.

The motion sensor 2 is of the 6-DOF mems type more fully explained in the previously referenced U.S. patent application Ser. No. 14/121,226. In the art, the term "6-DOF" refers to six degrees of freedom represented by the x, y, and z axis of movements. The term "mems" refers to miniature electrical mechanical systems. The motion parameters are sensed using acceleration sensors and gyroscope sensors for each axis which acceleration sensors and gyroscope sensors are integrated in the motion sensor 2.

Figure 3:
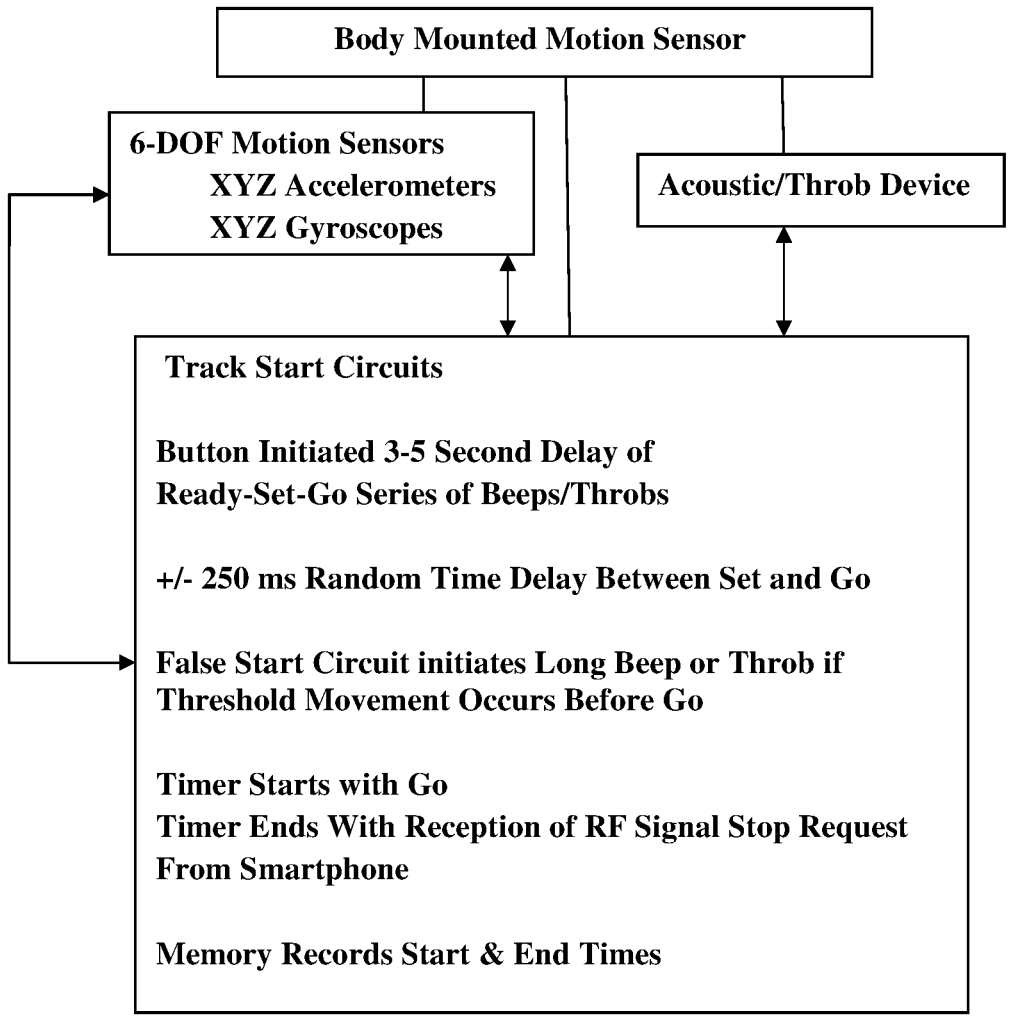
FIG. 3 is a flow chart showing the track start method.
Figure 4:
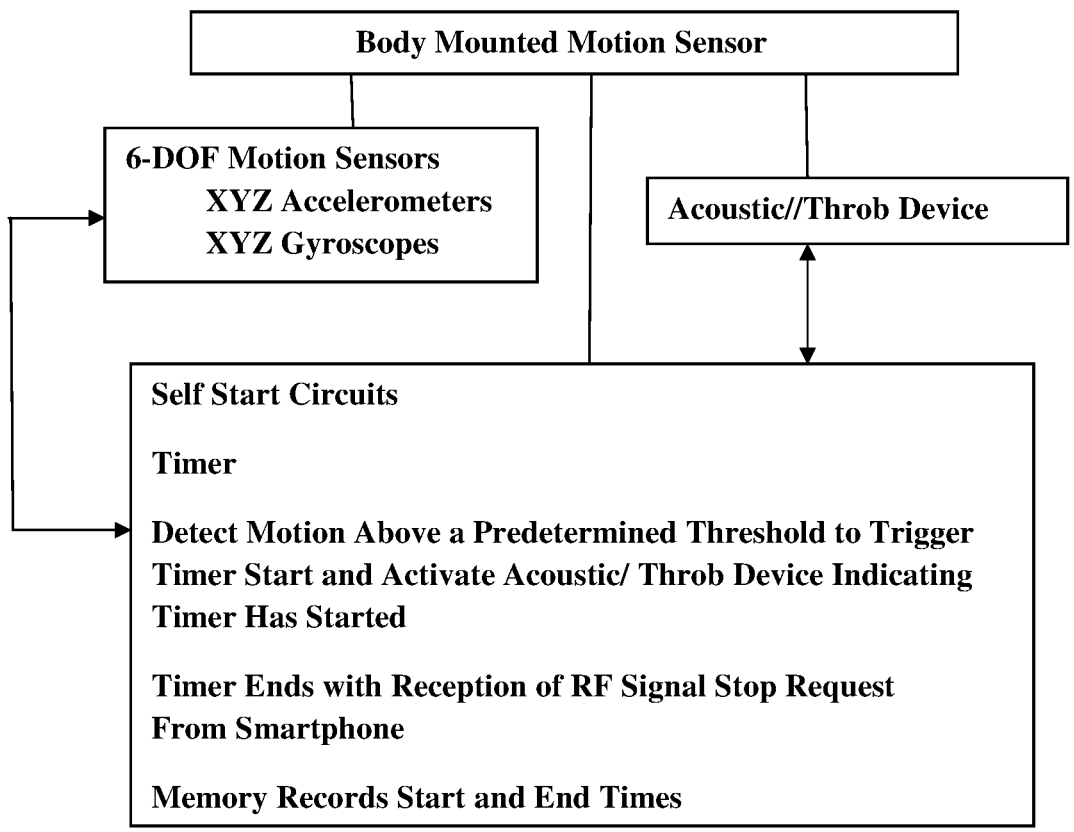
FIG. 4 is a flow chart showing the self-start method.

The athlete at the starting line chooses (see FIG. 2) between two ways to detect the start of the run event and thus save the event start time. A track start app as shown in FIG. 3 or a self start app as shown in FIG. 4 is chosen which apps are preloaded into the sensor 2 using the smartphone 3. An acoustic element is incorporated into the motion sensor 2 to provide acoustic feedback to the athlete as required by the particular exercise.

In the case of choosing the track start method, the athlete goes to the starting line and prepares to start the run by pushing a start button on the motion sensor to initiate a new run event. This activates a randomly variable delayed audible start signal such as a bell, whistle, or beeping sound. For example, once the button is pushed, after a 3-5 second delay the acoustic element emits a READY-SET-GO series of beeps. The time between the SET and GO beep is randomly varied by +/−250 milliseconds (ms). This delay is made random so that the sprinter does not try to anticipate the beep count. If the runner goes before the actual GO beep, a long beep is issued to indicate a false start, requiring the runner to reset and repeat the run start. The sensor start time is saved in the internal memory of the motion sensor 2 at the instant the GO peep is emitted, thus including the runner reaction time in the overall run time. The track start method yields the most accurate time as it includes the user reaction time as well as the run time.

In the case of choosing the self start method, the motion sensor 2 detects the run start instead of the READY-SET-GO method. The motion sensor 2 is configured though a memory to save the start time once the sensor detects motion above a pre-determined threshold. Once the threshold is exceeded, the start time is saved and a beep is issued to indicate to the user that the start was detected. If the runner goes and DOES NOT hear the beep, the threshold was not exceeded and the run start needs to reset. This method is not as accurate as the track start method due to the threshold delay in detecting the runner motion and does not include the runner reaction time from the GO beep to the run start.

By allowing the user to select which method to be used via the smartphone app, the user can select the start method. In both cases the end time is recorded the same as above described. The RF request stop signal is sent to the timer of the motion sensor 2. The motion sensor timer is started via the start event, either track starting or self starting, with the stop event being generated by the video trigger causing the smartphone to transmit the RF stop request with the motion sensor memory saving the time value on receipt of the RF stop request.

The difference in the start time recorded by the start event and the stop time recorded by the motion sensor on receipt of the RF stop signal request equals the run time. In testing, it was observed that an undetermined delay of up to 0-20 ms can occur. This delay occurs when the video trigger is generated and the RF stop request is actually sent via a BLE (Bluetooth Low Energy) interface or WiFi interface to the motion sensor 2. This is unavoidable due to the smartphone OS (Operating System) not being real time. An error compensated run time (shown in FIG. 2) is calculated from data developed at the factory manufacturing the motion sensor. The previously described "slap-sync" method is employed to determine and subtract the delay from the measured run time.

By using the "slap-sync" a simultaneous motion sensor and smartphone event is generated. The sensor time base is saved on receipt of the event and the smartphone app sends the RF request on receipt of the SAME event. If there were no delay in the RF request, the sensor time base would read zero. As it is, the stop RF request is delayed by a random 0-20 ms resulting in the time measured by the sensor time base to be 0-20 ms. By performing a series of theses calibration events, the true nature of the delay can be empirically determined and subtracted, eliminating or greatly reducing the unknown delay.

By performing a large number of trials at the factory, the average delay and the standard deviation of the delay can be characterized. It is important to note that this characterization is needed only once and can be applied to all sensor and smartphone app combinations. Individual calibration is NOT needed. This characterization is required for different operating systems (OS) such as the Apple iOS and the Android OS.

Once the characterization has been done for the Apple iOS and the Android OS, the AVERAGE value of the characterization delay is subtracted from the measured run time, leaving only the residual standard deviation (SD) as the error. For example, when this characterization has been done for the iOS it was found that the average delay was 12 ms with a SD measured as 8.5 ms. This results in a runtime uncertainty of +/−8.5 ms, which is below the required $\frac{1}{100}^{th}$ of a second timing resolution, essentially perfecting the motion sensor's time base.

In summary, the new run calibration routine burden associated with the "slap-sync" has been removed from the user by the one-time characterization of the particular OS delay above described.

In the case of a deaf athlete, the motion sensor 2 can be modified to set off vibration signals in place of the acoustic element as disclosed in FIG. 3 and FIG. 4.

The principles disclosed by the present invention may also be applied to other sports such as ice skating, roller skating, swimming, marathon running, soccer, basketball, bicycling events rowing, mountain climbing, skiing, snowboarding, skateboarding, crawling hazard obstacle course at military boot camp, hand over hand rope crossing and other extreme sport activities. Modified photo stamp time apps may be used to time each lap of such events. Of course, a water proof smart device and motion sensing monitor should be employed for a swimming event.

Although not shown, the tripod 4 of FIG. 1 may be replaced by a cylindrical open ended soft foam holder with the holder sides having rows of spaced slits thereon to accommodate the corners of various sizes smartphones. This has the added advantage of being able to use the foam cylinder as a protective packaging device for shipping the motion sensor 2 to the athlete.

In the "Clap-Sync Timers and Method" embodiment, an athlete measures sprint time for a fixed distance by locating the camera of a smartphone having a clap-sync app in alignment with the finish line. The smartphone saves a sprint end time recorded by a photo stamp time app. The athlete wearing a wrist mounted 6-DOF mems type motion sensor claps hands near the smartphone. The acoustic signal starts a smartphone's clock. Simultaneously, the sensor detects the clap's acceleration to start the sensors's free running clock while the smartphone's microphone detects the acoustic signal resetting to zero the respective clocks to synchronize both. The athlete at the starting line actuates the sensor's start button arming the sensor to detect the sprint's start time by detecting threshold motion parameters which start time is stored in the sensor's internal memory. Subtracting the synchronized start time saved in the motion sensor from the synchronized time saved in the smartphone gives the sprint time.

The athlete wears a wrist mounted 6-DOF mems type motion sensor, such as that disclosed in the above referenced U.S. patent application Ser. No. 14/121,226. When the athlete is finished prepositioning the smartphone, the athlete while near the smartphone claps hands to start synchronized timing of a crystal oscillator clock incorporated in the smartphone. The clap-sync app sets the clock to reset to zero. The microphone of the smartphone is used to detect the acoustic signal generated by the hand clap. The clapping motion is sensed by the motion sensor which via the acceleration associated with the handclap resets to zero a free running clock incorporated with the motion sensor. In this way, the clock of the smartphone and the clock of the motion sensor are simultaneously synchronized. The athlete then goes to the starting line and begins the training event. A timer incorporated with the motion sensor records the start time and is activated upon the motion sensor detecting threshold motion parameters indicating the start of the training event. The motion sensor records the starting time of the event and the camera of the smartphone records the finish time of the event. By knowing the synchronization time, the time used to traverse the premeasured distance is determined by subtracting the difference between the starting time and the synchronization time. This subtracted time represents the passage of time between the hand clapping and the start of the event during which the athlete has moved from the finish line to the starting line. The recorded starting time is transferred to the smartphone using a Bluetooth® or WiFi protocol. A computing app in the smartphone calculates the event time.

Figure 5:
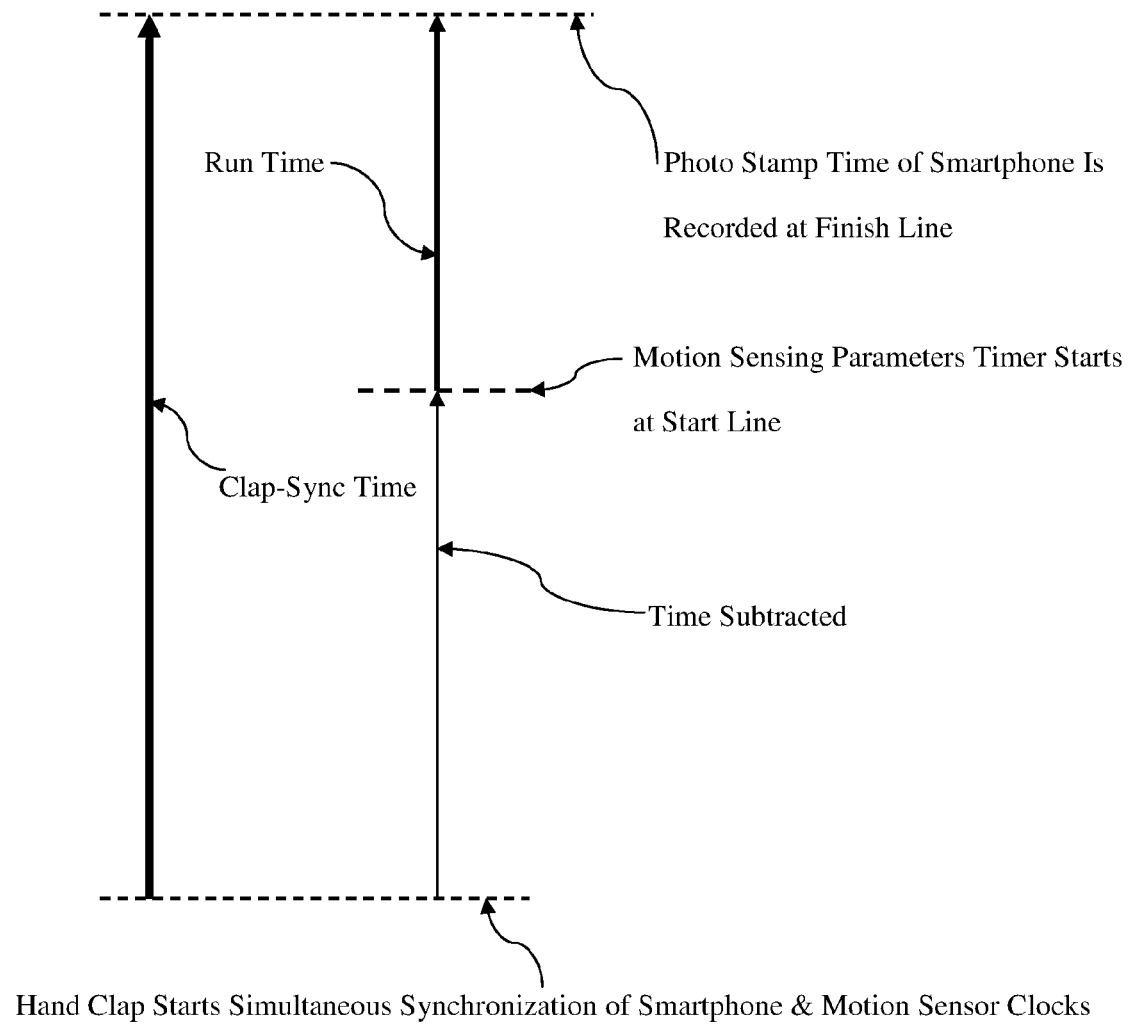
FIG. 5 is another embodiment depicting the time lines used to calculate the athlete's time to run the predetermined distance using a hand clap app installed in the athlete's smartphone.

Upon the athlete reaching the finish line, the smartphone's photo stamp time app records the end time of the sprint. FIG. 5 shows the time line of the synchronization time as the darkest line with the sprint time shown as a thinner line and the time elapsing between the start of the synchronization clocks and the start of the sprint as the thinnest line.

As an example of the method above outlined, the athlete synchronizes the crystal oscillator clock of the smartphone 3 and the clock of the motion sensor 2 by hand clapping to reset the clock times to zero. The athlete walks to the starting line and just before beginning the 40 yard sprint presses a motion sensing parameter on button for actuating the parameters being measured by the acceleration sensors and the gyroscopic sensors integrated with the motion sensor 2. Upon running movement of the athlete a starting time of 50 seconds is recorded. At the finish line, a finish time of 54.6 seconds is recorded by the smartphone using the photo stamp time app. The recorded starting time of 50 seconds is transferred by a Bluetooth or WiFi protocol to the smartphone which uses a computing app to determine the 40 yard sprint took the athlete 4.6 seconds to run. The time period passing from the clocks synchronization time of zero to the 50 second starting time is subtracted from the finish time to arrive at the 4.6 second sprint time.

The athlete uses a Bluetooth® protocol to transfer the motion parameters clock's start time to the smartphone. A Wi-Fi protocol may also be used to transfer the start time. The smartphone has a preloaded computing app which subtracts the time that has passed from the synchronization clap to the time of the run's start to give the time that has passed for the athlete to traverse the premeasured distance.

The principles disclosed by the present invention may also be applied to other sports such as ice skating, roller skating, swimming, marathon running and cycling events. Modified photo stamp time apps may be used to time each lap of such events. Of course, a water proof smart device and motion sensing monitor should be employed for a swimming event.

Various modifications to the preferred embodiments and the generic terms, principles, features and advantages of the present invention expressed in the written description and figures should not be limited to the exact construction and operation as illustrated and described. Many modifications, changes and equivalents will be readily apparent to those skilled in the art and are intended to fall within the scope of the invention which is not intended to be limited to the embodiments disclosed but is to be accorded the widest scope consistent with the principles and features described.

What is claimed is:

1. A method whereby an athlete accurately self-times a premeasured distance to be run by the athlete wherein the premeasured distance has a starting line and a finish line defining the premeasured distance comprising the athlete taking the steps of:
   (a) prepositioning at the finish line a smartphone having a camera;
   (b) loading the smartphone with a photo stamp time app to record the run's finish time;
   (c) wearing a motion sensor having a free running clock;
   (d) at the starting line initiating a delayed random 1-5 second starting signal to activate a timer of the motion sensor to record the start time of the run;
   (e) crossing the finish line to activate a video trigger of the photo stamp time app to send a RF stop signal from the smartphone to the timer of the motion sensor to record finish time; and
   (f) transferring the start time and finish time from the motion sensor to the smartphone to determine run time.

2. The method of claim 1 further including the step of wearing the motion sensor on a wrist of the athlete.

3. The method of claim 1 wherein the step of activating at the starting line the timer of the motion sensor includes sensing of at least one threshold biometric motion parameter using a six degrees of freedom (6-DOF) Micro Electro Mechanical System (MEMS) motion sensor.

4. The method of claim 1 wherein the step of determining the run time further includes subtracting a predetermined average delay time based on the operating system of the smartphone to compensate for real time error introduced by a time delay between the video trigger being activated and the sending of the RF stop signal from the smartphone to the motion sensor.

5. The method of claim 1 wherein the athlete preselects to start the timer a track start READY-SET-GO series of beeps to initiate the 1-5 second random delayed starting signal by pushing a button on the motion sensor.

6. A method whereby an athlete accurately self-times a premeasured distance to be traversed by the athlete wherein the premeasured distance has a starting point and a finish point defining the premeasured distance comprising the athlete taking the steps of:
   (a) prepositioning at the finish point a smartphone having a crystal oscillator clock and a camera;
   (b) loading the smartphone with a photo stamp time app to record the athlete's finish time at the finish point;
   (c) wearing a motion sensor having a free running clock;
   (d) at the starting point initiating a delayed random 1-5 second starting signal to activate a timer in the motion sensor to record the start time of the starting signal;

(e) crossing the finish point to activate a video trigger of the photo stamp app to send a RF stop signal from the smartphone to the timer of the motion sensor to record finish time; and (f) transferring the start time and finish time from the motion sensor to the smartphone determining the time it took for the athlete to traverse the premeasured distance.

7. The method of claim 6 wherein the step of transferring the recorded start time from the motion sensor to the smartphone is done using a Bluetooth or WiFi protocol.

8. The method of claim 6 wherein the step of activating at the starting point the timer of the motion sensor includes sensing of at least one threshold biometric motion parameter using a 6-DOF MEMS sensor of the motion sensor.

9. The method of claim 6 wherein the athlete traverses the premeasured distance by the physical act of one of running, ice skating, roller skating, swimming, bicycling, broad jumping, skiing, snowboarding, canoeing, climbing, crawling or hand over hand rope crossing.

10. The method of claim 6 wherein the step of determining the time to traverse the premeasured distance further includes subtracting a predetermined average delay time based on the operating system of the smartphone to compensate for real time error introduced by a time delay between the video trigger being activated and the sending of the RF stop signal from the smartphone to the motion sensor.

11. The method of claim 6 wherein the athlete preselects to start the timer a start READY-SET-GO series of beeps to initiate the 1-5 second random delayed starting signal by pushing a button on the motion sensor.

12. A body mounted motion sensor for an athlete training for a racing event comprising:
(a) a 6-DOF MEMS motion sensor;
(b) an acoustic or silent throbbing device;
(c) a starting signal circuit to activate the acoustic or throbbing device in a racing READY-SET-GO series of beeps or throbs with the last beep the loudest or throb the hardest to signal the GO to start the racing event with the starting signal circuit having a random variance of a few seconds between the SET and GO beeps or throbs.

13. The body mounted motion sensor of claim 12 further including the random variance set between the SET and GO beeps or throbs being +/−250 ms.

14. The body mounted motion sensor of claim 12 further including a motion sensor button having a circuit which provides a 3-5 second delay before initiating the READY-SET-GO series of beeps or throbs.

15. The body mounted motion sensor of claim 12 further including a false start circuit which is activated by the 6-DOF MEMS motion sensor sensing a threshold motion above a pre-determined threshold before the GO beep or throb occurs.

16. The body mounted motion sensor of claim 12 further including a memory to record the time of the start of the racing event at the instant the GO beep or throb is emitted.

17. The body mounted motion sensor of claim 12 further including a timer activated by the GO beep or throb and stopped by the reception of a RF halt signal signifying the end of the racing event.

18. A method whereby an athlete accurately self-times a premeasured distance to be run by the athlete wherein the premeasured distance has a starting line and a finish line defining the premeasured distance comprising the steps of:
(a) prepositioning at the finish line a smartphone having a crystal oscillator clock and a camera;
(b) loading the smartphone with a photo stamp time app to record the run's finish time
(c) loading the smartphone with a clap-synchronizing timer app;
(d) wearing a motion sensor having a free running clock;
(e) using the athletes hands to clap in the vicinity of the smartphone while wearing the motion sensor thereby synchronizing both clocks to establish a synchronization time;
(f) at the starting line activating a timer of the motion sensor to record the start time of the run;
(g) crossing the finish line to activate the photo stamp time app to provide the finish time of the run;
(h) transferring the recorded time of the start of the run to a computing app on the smartphone; and
(i) using the computing app on the smartphone to compute the run time by subtracting the time passing between the time of synchronization and the start of the run time from the finish time of the run.

19. The method of claim 18 wherein the synchronization of the free running clock is based on the motion sensor detecting the acceleration of the clapping hands and the synchronization of the crystal oscillator clock of the smartphone is based on a microphone of the smartphone detecting the acoustic signal of the hands being clapped.

20. A method whereby an athlete accurately self-times a premeasured distance to be traversed by the athlete by running, swimming, skating or cycling or combination thereof wherein the distance includes at least one lap having a starting point and a finish point defining the premeasured distance comprising the steps of:
(a) prepositioning at the finish point a smartphone having a settable clock and a camera;
(b) loading the smartphone with a photo stamp time app to record the athlete's finish time at the finish point;
(c) loading the smartphone with a sound-synchronizing timer app;
(d) wearing a motion sensor having a settable clock;
(e) producing a sound near the smartphone using the hands of the athlete while wearing the motion sensor to thereby synchronize both clocks to establish a synchronization time;
(f) at the starting point activating a timer of the motion sensor to record the start time of the premeasured distance to be traversed;
(g) reaching the finish point to activate the photo stamp time app to provide the finish time of the predetermined distance to be traversed;
(h) transferring the recorded start time to a computing app on the smartphone; and
(i) using the computing app to compute the time for traversing the premeasured distance by subtracting the time passing between the time of synchronization and the start time from the finish time.

* * * * *